United States Patent [19]
Dysarz

[11] Patent Number: 5,180,369
[45] Date of Patent: Jan. 19, 1993

[54] SELF DESTRUCTIVE SAFETY SYRINGE

[76] Inventor: Edward D. Dysarz, 11423 Triola La., Houston, Tex. 77072

[21] Appl. No.: 827,366

[22] Filed: Jan. 20, 1992

[51] Int. Cl.$^5$ ............................................. A61M 5/00
[52] U.S. Cl. .................................... 604/110; 604/195
[58] Field of Search ............... 604/110, 195, 198, 263, 604/187

[56] References Cited

U.S. PATENT DOCUMENTS

| | | | |
|---|---|---|---|
| 4,966,592 | 10/1990 | Burns et al. | 604/198 |
| 4,973,316 | 11/1990 | Dysarz | 604/195 |
| 5,049,133 | 9/1991 | Pascual | 604/110 |
| 5,084,018 | 1/1992 | Tsao | 604/110 |
| 5,088,986 | 2/1992 | Nusbaum | 604/195 |
| 5,092,853 | 3/1992 | Couvertier, II | 604/110 X |

Primary Examiner—John D. Yasko
Attorney, Agent, or Firm—Derek R. Van Gilder

[57] ABSTRACT

A self destructive safety syringe assembly having a needle cannula fixed to a slideable piston. The slideable piston and slideable piston flange are held within the first barrel of the syringe assembly by a compressed spring, a guide tube and a shatter ring. The hollow elongated plunger of the syringe assembly is a hollow elongated tube with a thumb flat at one end, a sliding gasket, a plunger shatter plate and a hook rim at the other end. When medicament is injected into a body the elongated hollow plunger is further thrust into the shatter ring, the shatter ring shatters, or breaks or fails further allowing the slideable piston and slideable piston flange to thrust into the plunger shatter plate thus causing the plunger shatter plate to shatter, or fail or break. This action further causes the slideable piston and needle cannual to be thrust into the elongated hollow plunger by the spring and wherein the spring will further prevent the slideable piston and needle cannula from re-entering the guide tube and further rendering the syringe unuseable and completely destroyed internally. The needle cannula is further completely contained within the elongated hollow plunger wherein it cannot touch, prick or injure another or further inject a disease into others.

15 Claims, 4 Drawing Sheets

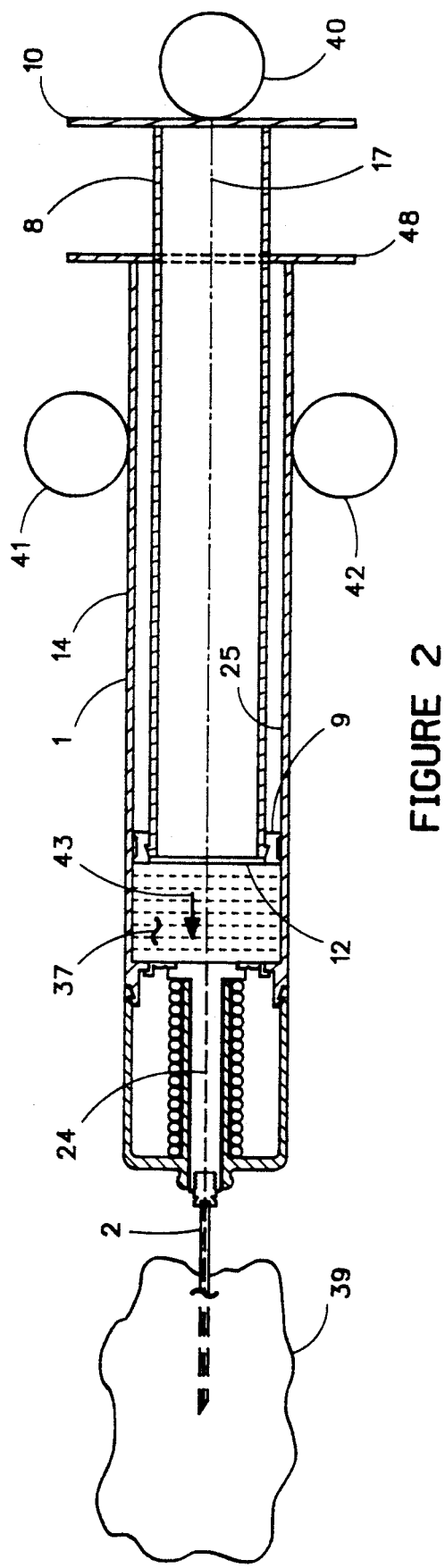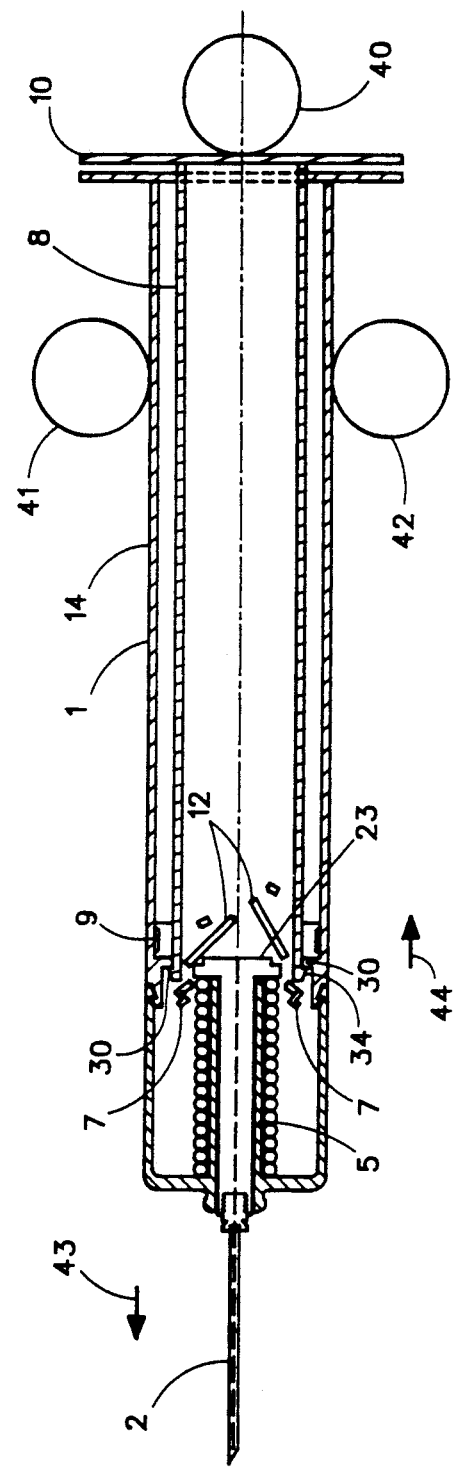
FIGURE 2
FIGURE 3

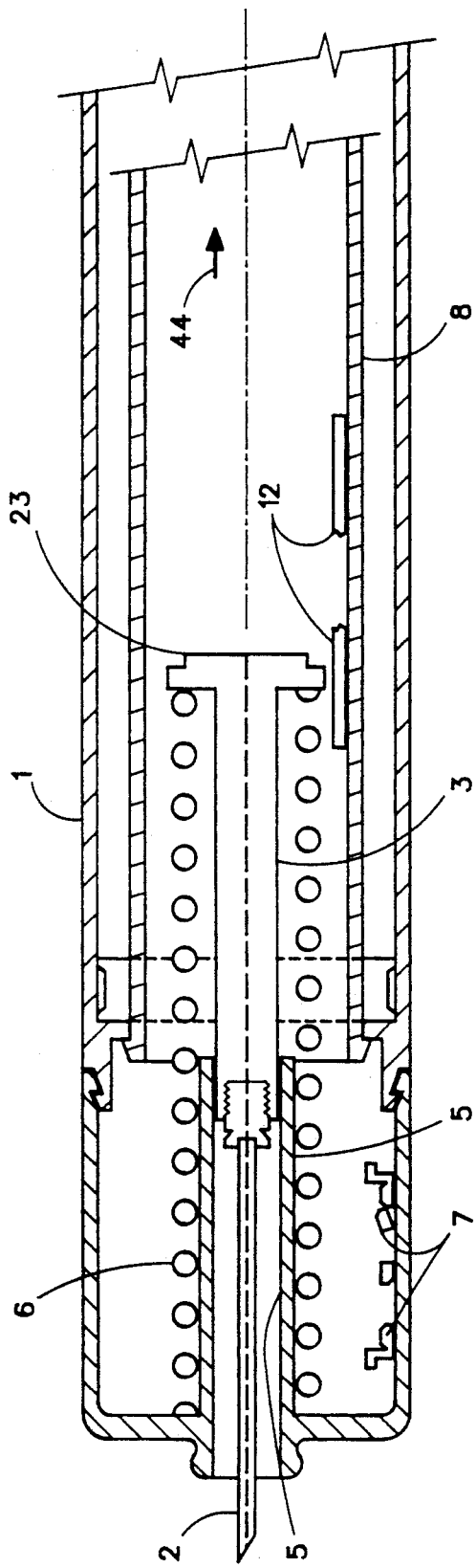
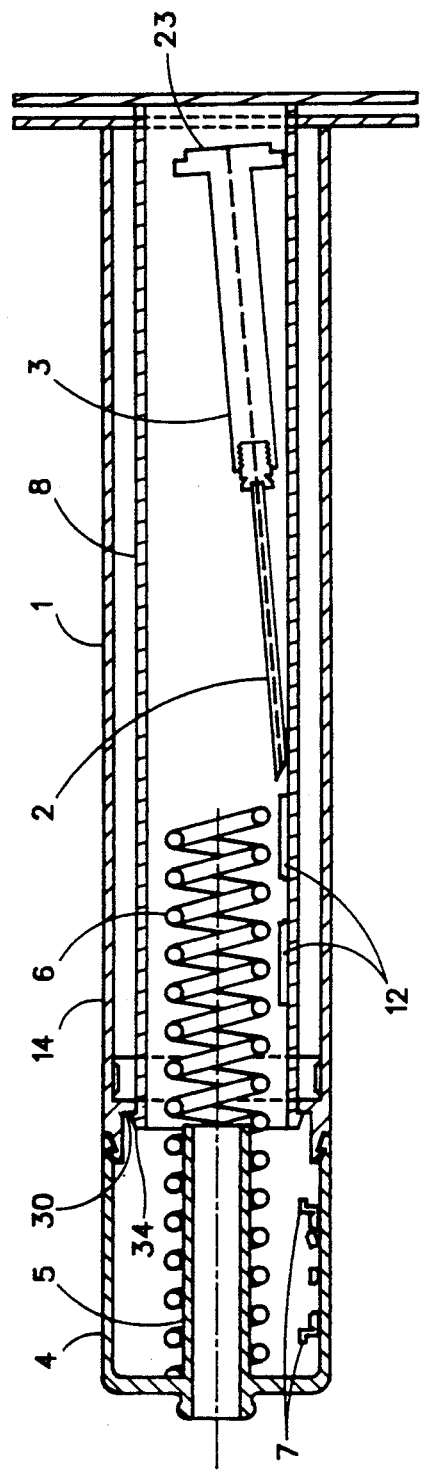
FIGURE 4
FIGURE 5

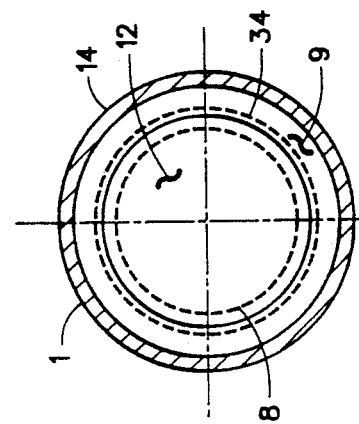
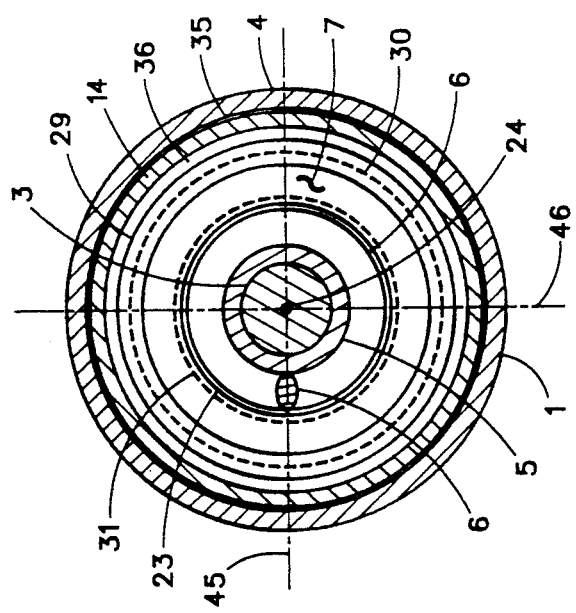
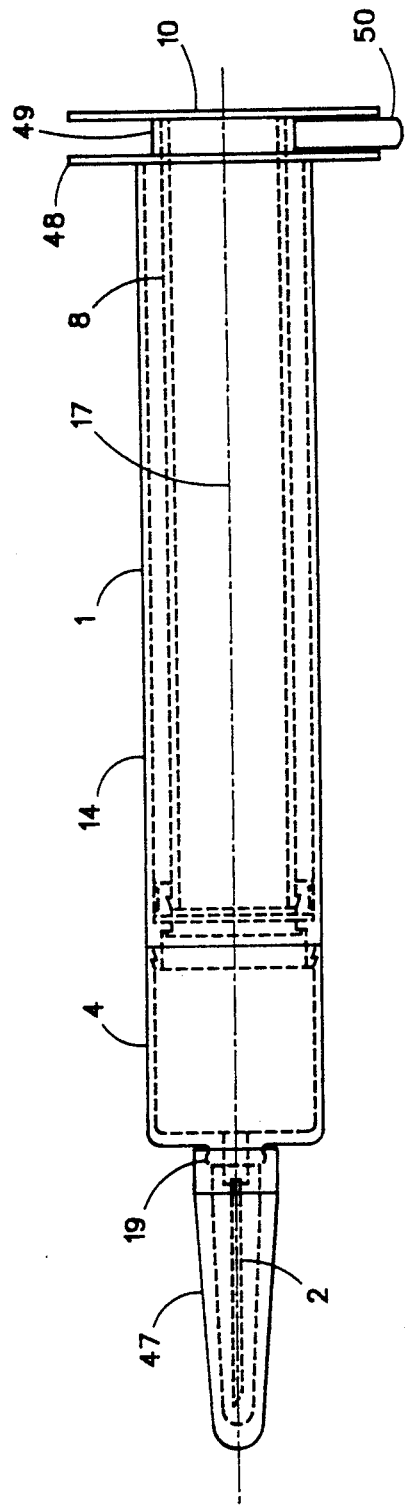
FIGURE 7
FIGURE 6
FIGURE 8

SELF DESTRUCTIVE SAFETY SYRINGE

BACKGROUND OF THE INVENTION

There are many safety syringe designs available today. Some of these designs have a sleeve or a sheath that will cover the needle after is has been used. Some typical designs with sleeves or sheaths are Z. M. ROEHR, et al U.S Pat. No. 3,008,570, Z. M. ROEHR U.S. Pat. No. 3,107,785, BARTNER, et al U.S. Pat. No. 3,895,633, G. K. BURKE U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 4,666,435, SPENCER U.S. Pat. No. 4,702,738, MILORAD U.S. Pat. No. 4,702,739, SPENCER U.S. Pat. No. 4,801,295, PONCY U.S. pat. No. 4,816,022, and HUGHES U.S. pat No. 4,840,619.

Other designs have a retractable needle such as WELTMAN U.S. Pat. No. 3,306,290, HAINING U.S. Pat. No. 4,790,822, and DENT U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Most of these designs have one major purpose and that is to prevent the spread of infectious diseases such as AIDS, hepatitis or other diseases from an accidental injection with a contaminated needle, into others after the needle of the syringe was inserted into a patient with one of the above mentioned diseases. These various designs of safety syringes all work well up to a degree, but they all fall short of the intended purpose during the act of covering the needle, or removing the needle.

All of these syringe designs require at least two hands to operate. The use of two hands to cover the contaminated needle is most unsatisfactory in that during the act of placing a second hand on the syringe the person holding the syringe in one hand may be bumped and accidently inject the needle into their other hand before the syringe can be grasped. Other accidental jabbings or injections can happen in an ambulance where just as a person tries to grasp the contaminated syringe, the ambulance can hit a bump in the road causing the person holding the syringe to accidentally stick another person or themselves with the contaminated needle. The need has developed for a syringe that will cover the contaminated needle with the use of only one hand.

There are still other types of safety syringes that are available today such as DYSARZ U.S. Pat. No. 4,973,316 and again by DYSARZ et al. U.S. Pat. No. 4,978,343 that can be operated by one hand and are further retractable, however, they are not destroyed internally. In DYSARZ, to compress the plunger to disable the syringe one must overcome the energy of a spring in order to retract the needle cannula of the syringe. There is no need to overcome the spring energy in the design of the present invention.

SUMMARY

It is the object of the present invention to provide a syringe that cannot be used a second time after it has been used once by destroying the vital internal parts after only one use.

Another object of the present invention is to provide a syringe wherein the needle cannula of the syringe is retracted into the plunger of the syringe and protected from an accidental sticking after it has been used and contaminated.

Another object of the present invention is to provide a one handed retractable syringe wherein the needle cannula is caused to retract with very little pressure required from the thumb on the plunger to break the shatter ring, and further disable the syringe.

It is another object of the present invention to render the syringe not only useless after being used once, but to internally destroy the syringe rendering it almost impossible to repair or put back together again.

It is yet another object of the present invention to further render the syringe unuseable by internally locking the plunger within the barrel of the syringe forcing a person to rip or break apart the syringe to reuse the needle and, thereby, further destroy the syringe.

It is still yet another object of the present invention to prevent any fluid from leaking out of the syringe after it has been used.

The foregoing and other objects and advantages are attained with a hypodermic syringe assembly comprised of a hollow elongated barrel, an elongated hollow plunger, a needle cannula, a slideable piston shatter plate, an elongated plunger shatter plate, a guide tube and plunger hook rim in combination with a spring. This assembly is used to inject a medicament, drug or other material into a human patient, an animal or other object. The slideable piston shatter plate and the plunger shatter plate are shattered and the spring further thrusts the needle cannula fixed to the slideable piston into the elongated hollow plunger and further locking the plunger hook rim onto the elongated hollow barrel flange thus placing the contaminated needle into a locked container and further rendering the syringe unuseable.

The features of the present invention can best be understood together with further objects and advantages by reference to the following description taken in conjunction with the accompanying drawings wherein like numerals indicate like parts.

BRIEF DESCRIPTION OF THE DRAWINGS

FIG. 2 is a section elevation of the entire syringe assembly while medicament is being injected into a patient.

FIG. 3 is a section elevation view to the syringe assembly showing the plunger shatter plate and the piston shatter ring being shattered.

FIG. 4 is an enlarged partial section elevation view of the syringe assembly showing the slideable piston and the needle cannula being thrust into the elongated hollow plunger.

FIG. 5 is a section elevation showing needle cannula and the slideable piston at rest inside of the elongated hollow plunger.

FIG. 6 is a section view taken through FIG showing the various internal elements of the syringe assembly and their relationship to each other.

FIG. 7 is another section view as taken through FIG 1 showing various internal elements of the syringe assembly and their relationship with each other.

FIG. 8 is an outside elevation of the syringe showing the pull off band and the needle cannula double cover.

DETAILED DESCRIPTION OF THE PREFERRED EMBODIMENT

Figure 1:
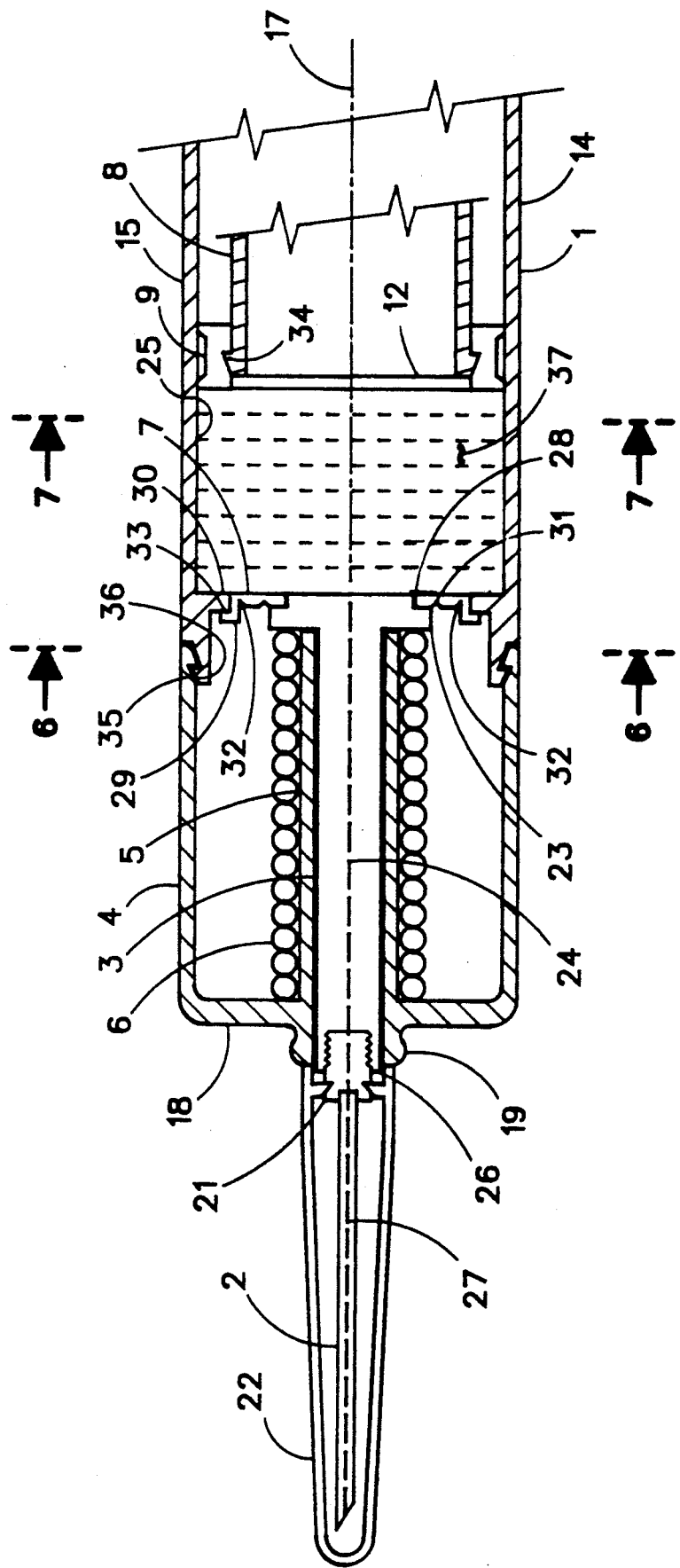
FIG 1 is an enlarged section elevation describing all of the internal components of the syringe assembly.

Referring to FIG 1, there is shown an enlarged partial section elevation of the self destructive safety syringe also referred to as the syringe assembly 1.

The syringe assembly 1 is shown with a needle cannula 2 with a cannula 27 formed in the needle cannula 2. The needle cannula 2 has a point at the first end and is further shown fixed to a needle cannula foundation 21 at the second end of the needle cannula with adhesive or friction or some other suitable means. Also shown connected to the needle cannula foundation 21 is the needle cannula cover 22, which can be removed prior to using the syringe assembly 1.

The needle cannula foundation 21 is further fixed to the slidable piston 3 with threads 26 or some other suitable means not shown. The slidable piston 3 has a slidable piston cannula 24 that is a continuation of the cannula 27 of the needle cannula 2. The slidable piston 3 has a first end wherein the needle cannula foundation 21 is fixed. A slidable piston flange 23 is fixed to the second end of the slideable piston 3. The slidable piston flange 23 has a first side touching the spring 6 and a second side that comes in contact with the medicament 37. The slidable piston 3 is held and laterally supported and contained within a guide tube 5. The guide tube 5 will allow the slidable piston 3 to move parallel to the longitudinal axis 17 only which will be explained later.

The guide tube 5 is shown suitably fixed to the inside of the first barrel flange 18 at the first end of the guide tube 5. The second end of the guide tube 5 is near or even touching the first side of the slidable piston flange 23. The slidable piston 3 is contained and guided by the inside surface of the guide tube 5 and the spring 6 is also contained and guided by the outside surface of the guide tube 5. The first barrel flange 18 forms part of a cover at the first end of the first barrel 4. The first barrel flange 18 has an inside and an outside. The inside is shown as a base for the spring 6 and the outside is fixed to the cover snap flange 19. The first barrel flange 18 further has an opening formed in its center extending from its inside through its outside to accommodate the slideable piston 3. The opening is larger than the slideable piston 3. The first barrel 4 is a container or cover for the spring 6, the guide tube 5, the slidable piston 3 and the slidable piston flange 23. The first barrel 4 has a first and a second end. The first end of the first barrel 4 is shown fixed to the first barrel flange 18. Near the second end of the first barrel 4, there is shown a V ring groove 35 formed to receive the latch barb 36, which is at the first end of the elongated hollow barrel 14. During the assembly of the elongated hollow barrel 14 to the first barrel 4, the V ring groove 35 is snapped into the latch barb 36, thus locking the elongated hollow barrel 14 to the first barrel 4, to where they cannot be separated, unless they are broken. Adhesive can also be used to fix the two units together, if desired. The V ring groove 35 and the latch barb 36 are shown to extend around the entire circumference of the elongated hollow barrel 14 and the first barrel 4 but they may only extend partially around the circumference by design choice.

The spring 6 is shown compressed between the inside of the first barrel flange 1B and the first side of the slidable piston flange 23.

The slideable piston flange 23 is restrained from being thrust into the elongated hollow barrel 14 and elongated hollow plunger 8 by the slidable piston shatter plate 7 that has a first side and a second side that is further restrained from thrusting into the elongated hollow barrel 14 by the shatter ring flange 29 thrusting or pushing on the first side of the elongated hollow barrel flange 30 that extends inward toward the longitudinal axis 17 from the elongated hollow barrel inner surface 25 of the elongated hollow barrel 14. The second side of the elongated hollow barrel flange 30 is in contact with the medicament 37. It should be noted that the slidable piston flange 23 could be one piece and extend from the slidable piston 3 to overlap the elongated hollow barrel flange 30. As it is shown, the slidable piston flange 23 is held to the first side of the slidable piston shatter plate 7 by the compression of the compressed spring 6, thus forming a liquid tight and gas tight seal by the slidable piston flange gasket 28 or a suitable adhesive by design choice. The liquid tight and gas tight connection between the shatter ring flange 29 and the elongated hollow barrel flange 30 is made by the shatter ring flange gasket 33 or a suitable adhesive by design choice.

The slideable piston shatter plate 7 is shown with an inner V groove 31 and an outer V groove 32 that will allow the slideable piston shatter plate 7 to be shattered or broken more easily, which will be shown in FIG. 3. The slideable piston shatter plate 7 could be made out of a brittle plastic or glass with or without the V grooves by design choice.

The elongated hollow barrel 14 is shown with an inner surface 25 and an outer surface 15. The longitudinal axis 17 is shown at the center of the elongated hollow barrel 14 and could extend the entire length of the self syringe assembly 1 from the needle cannula 2 through the elongated hollow barrel 14.

The first end of the elongated hollow plunger 8 is shown inside of the elongated hollow barrel 14. The elongated hollow plunger 8 has an inside which in FIG I is shown empty. The elongated hollow plunger 8 has an outside that is nearer to the inside surface of the elongated hollow barrel 14. The sliding gasket 9 shown at the first end of the elongated hollow plunger 8 is made out of rubber or other suitable material and it extends over the entire circumference of the elongated hollow plunger 8 to further form a liquid tight seal and a gas tight seal between the elongated hollow plunger 8 and the elongated hollow barrel inner surface 25.

At the first end of the elongated hollow plunger 8 there is shown the plunger shatter plate 12 with a first side and a second side that is either held to the first end of the elongated hollow plunger 8 by the sliding gasket 9 or adhesive or some other suitable means. The plunger shatter plate 12 is shown as being round, but it could be any shape by design choice and it is made out of glass, brittle plastic or some other suitable material. The plunger shatter plate 12 could also be part of the elongated hollow plunger 8. The plunger shatter plate 12 touches the elongated hollow plunger 8 at the second side of the plunger shatter plate 12.

On the first end of the elongated hollow plunger 8, there is also shown a plunger hook rim 34. The elongated hollow plunger hook rim 34 extends around all of or part of the outside surface and first end of the elongated hollow plunger 8 and is designed to snap or be caught on the elongated hollow barrel flange 30 when the syringe assembly 1 is fully compressed. The plunger hook rim 34 has a first end and a second end and it slopes from the longitudinal axis 17 toward the elongated hollow barrel inner surface 11 at the second end of the plunger hook rim 34. The plunger hook rim 34 is essentially perpendicular to the longitudinal axis 17 at the second end of the plunger hook rim 34 which will enable the plunger hook rim 34 to be moved past the elongated hollow barrel flange 30 and to further be caught on the first side of the elongated hollow barrel flange 30 which will be explained later.

Also, shown contained between the slidable piston flange 23, the second side of the slidable piston shatter plate 7, the elongated hollow barrel flange 30, the elongated hollow barrel inner surface 25, the sliding gasket 9 and the first side of the plunger shatter plate 12 is the medicament 37 or other suitable material.

On the outside of the first barrel flange 18 is the cover snap flange 19 that will further allow a cover to be placed over the needle cannula 2 and or the needle cannula cover 22.

Referring to FIG. 2, there is shown another section elevation of the syringe assembly 1.

The needle cannula cover 22 has been removed and the needle cannula 2 is shown inserted into a body 39 or part of a body or other suitable location. The medicament 37 is being injected through the slidable piston cannula 24 and the needle cannula 2 and into the body 39 of the patient.

The medicament 37 is being forced or pumped under pressure by a thumb 40 pressing on the thumb flat 10 while the elongated hollow barrel 14 is suitably held between first finger 41 and second finger 42. As the thumb 40 presses on the thumb flat 10, the elongated hollow plunger 8, in combination with, the plunger shatter plate 12 and the sliding gasket 9, forming a liquid tight and gas tight seal on the elongated hollow barrel inner surface 25, is pushed in a needle cannula direction 43, forcing the medicament 37 into the needle cannula 2 and into the body 39.

The second end of the first barrel 4 is shown fixed to the first end of the elongated hollow barrel 14. A plunger guide flange 48 is shown at the second end of the elongated hollow barrel 8. The plunger guide flange 48 circumferentially extends from the outside of the elongated hollow barrel 14 towards the longitudinal axis 17 and ends near the elongated hollow plunger 8 wherein the plunger guide flange 48 guides the elongated hollow plunger 8 and further keeps the elongated hollow plunger 8 in alignment with the longitudinal axis 17.

Referring to FIG. 3, there is shown another section elevation of the syringe assembly 1 of the preferred embodiment.

After the medicament has been injected into the body or part of the body, the needle cannula 2 could still be in the body, but in this case, it has been withdrawn from the body, which will be by user's choice.

The elongated hollow barrel 14 is still being suitably held between the first finger 41 and the second finger 42 and the thumb 40. The thumb 40 is shown still pressing on the thumb flat 10, forcing the elongated hollow plunger 8 to push the plunger shatter plate 12 into the slideable piston shatter plate 7, the slideable piston shatter plate 7 is shattered, broken or failed, thus releasing the slideable piston flange 23 from the elongated hollow barrel flange 30.

As the elongated hollow plunger 8 is further pushed in the needle cannula direction 43, the plunger shatter plate 12 is thrust into the slideable piston flange 23 which is further restrained from moving in the needle cannula direction 43 by the guide tube thus causing the plunger shatter plate 12 to shattered on the slideable piston flange 23.

As the slideable piston shatter plate 7 and the plunger shatter plate 12 is being shattered, the sliding gasket 9 is being held on the elongated hollow barrel flange 30 and is further moved in a thumb flat direction 44 relative to the thumb flat 10 thus forcing the plunger hook rim 34 to move past the elongated hollow barrel flange 30 wherein the perpendicular end at the second end of the plunger hook rim 34 will get snapped or locked onto the first side of the elongated hollow barrel flange 30.

Referring to FIG. 4 there is shown an enlarged section elevation of the syringe assembly 1 of the preferred embodiment after the internal parts of the syringe assembly 1 have been destroyed.

After the slideable piston shatter plate 7 is shattered by the first end of the elongated hollow plunger 8 and the plunger shatter plate 12 is shattered by the slideable piston flange 23 the slideable piston flange 23 is no longer restrained and the spring 6 that was shown compressed in FIG FIG. 2 and FIG. 3 is now allowed to thrust on and propel the slideable piston flange 23, the slideable piston 3 and the needle cannula 2 into the inside of the elongated hollow plunger 8. As the slideable piston 3 is propelled in a thumb flat direction 44 it is guided on the inside surface of the guide tube 5 further forcing the slideable piston 3 to move parallel to the inside of the guide tube 5 and thereby preventing the needle cannula 2 from touching any exterior portion of the syringe assembly I in the area of the cover snap flange 19 as the needle cannula 2 is shot into the elongated hollow plunger 8 thus preventing any body fluids containing diseases, etc. that may be on the needle canula 2 from being transferred to any exterior portion of the syringe assembly I.

Referring to FIG. 5, there is shown a section elevation of the syringe assembly 1 with the needle cannula 2 and the slideable piston 3 inside of the elongated hollow plunger 8.

When the slideable piston 3, the needle cannula 2 and the slideable piston flange 23 come to rest inside of the elongated hollow plunger 8 they are prevented from reentering the guide tube 5 because the spring 6 is now expanded to where the needle cannula 2 cannot pass through the guide tube 6.

The elongated hollow plunger 8 cannot be withdrawn from the elongated hollow barrel 14 because the second end of the plunger hook rim 34 is now locked onto the elongated hollow barrel flange 30 and the syringe assembly 1 would nave to be further destroyed to get the elongated hollow plunger out of the elongated hollow barrel 14.

Parts of the slideable piston shatter plate 7 and the plunger shatter plate 12 are shown broken up or shattered within the elongated hollow plunger 8 and the first barrel 4. The slideable piston shatter plate 7 would most likely be broken along the inner V groove and/or the outer V groove.

Referring to FIG. 6 there is shown a section view of the syringe assembly I as taken through FIG. 1.

Near the outside of the syringe assembly I there is shown the part of the V ring groove 35 which is part of the first barrel 4. The latch barb 36 is shown as part of the elongated hollow barrel 14.

In FIG. 6, the spring 6 is called out twice, once as a section view since the spring must be cut by the section line and the other spring 6 is shown as the spring 6 in plain view. Part of the slideable piston flange 23 is shown next to the spring 6.

The elongated hollow barrel flange 30 is shown as hidden lines behind the shatter ring flange 29.

The slideable piston cannula 24 is shown inside of the slideable piston 3. The slideable piston 3 is shown inside of the guide tube 5.

The slideable piston shatter plate 7 is shown with the inner V groove 31. The outer V groove cannot be seen in this view because of its proximity to the edge of the shatter ring flange 29.

The longitudinal axis is where the center line X 45 crosses the center line Y 46 and would be the center of the slideable piston cannula 24.

Referring to FIG. 7 there is shown a section view of the syringe assembly 1 as taken through FIG. 1.

The elongated hollow barrel 14 is shown on the outside, the slideable gasket 9 is shown between the inside surface of the elongated hollow barrel 14 and the plunger shatter plate 12. The first end of the elongated hollow plunger 8 is shown with hidden lines. The plunger hook rim 34 is also shown with hidden lines.

Referring to FIG. 8 there is shown an outside elevation of the syringe assembly 1 as it would be stored on the shelf or shipped prior to using.

A second cover cap 47 is shown covering the needle cannula 2 and is held onto the syringe assembly 1 by the cover snap flange 19.

The first barrel 4 is shown fixed to the first end of elongated hollow barrel 14. At the second end of the elongated hollow barrel 14 there is shown the plunger guide flange 48 that circumferentially extends from the outside of the elongated hollow barrel 14 past the elongated hollow barrel 14 towards the longitudinal axis 17 to a point near the elongated hollow plunger 8 wherein the plunger guide flange 48 guides the second end of the elongated hollow plunger 8, to allow the elongated hollow plunger 8 to freely move in and out of the elongated hollow barrel 14 but will keep the elongated hollow plunger 8 aligned with the elongated hollow barrel 14 and the longitudinal axis 17.

Shown between the plunger guide flange 48 and the thumb flat 10 is a stop ring 49. The stop ring 49 is a flexible ring with a first end and a second end that is wrapped around the circumference of the elongated hollow plunger 8 to prevent the elongated hollow plunger 8 from being accidentally depressed and thereby causing the self destructive safety syringe from self destructing. The stop ring 49 is removed by pulling the stop ring tab 5 and unwinding the stop ring 49 from the outside circumference of the elongated hollow plunger 8.

The stop ring 49 and the tab 50 are made out of plastic or some other suitable, flexible material.

Although the system described in detail supra has been found to be most satisfactory and preferred, many variations are possible. For example, the first barrel could be threaded on to the elongated hollow barrel, the syringe could be made out of glass, or the needle cannula could be fitted to the slideable plunger by an adhesive or friction by design choice.

Although the invention has been described with reference to the preferred embodiment, it will be understood by those skilled in the art, that additions, modifications, substitutions, deletions and other changes not specifically described, may be made in the embodiments herein. It should be understood that the details herein are to be interpreted as illustrative and are not in a limiting sense.

What is claimed as invention is:

1. A syringe assembly held by fingers and thumb for injecting medicament or fluid into a body or part of a body comprising:

a needle cannula with a first end and a second end, wherein there is a point at said first end and wherein there is a cannula formed in said needle cannula that extends from said first end through said second end;

a slideable piston with a first end and a second end, wherein said second end of said needle cannula is fixed to said first end of said slideable piston and wherein said slideable piston further has a cannula formed in said slideable piston whereby said cannula extends from said first end of said slideable piston through said second end of said slideable piston and is further connected with said cannula of said needle cannula;

a slideable piston flange with a first side and a second side, wherein said first side of said slideable piston flange is fixed to said second end of said slideable piston, and wherein a cannula is formed in said slideable piston flange that connects with said cannula in said slideable piston and wherein said cannula in said slideable piston flange extends from said first side through said second side of said slideable piston flange;

a guide tube with a first end and a second end and an inside surface and an outside surface, wherein said slideable piston is laterally held by said inside surface of said guide tube and said slideable piston is laterally supported by said inside surface of said guide tube and wherein said second end of said guide tube is near said slideable piston flange;

a first barrel flange with an inside and an outside side, whereas said inside of said first barrel flange is fixed to said first end of said guide tube and said outside of said first barrel flange is nearer to said needle cannula;

a first barrel with a first end and a second end, wherein said first end of said first barrel is fixed to said inside of said first barrel flange;

an elongated hollow barrel with a first end and a second end and an inside surface and an outside surface, wherein said elongated hollow barrel is suitably fixed to said second end of said first barrel at said first end of said elongated hollow barrel and wherein said elongated hollow barrel further has a longitudinal axis in the center of said elongated hollow barrel;

an elongated hollow barrel flange with a first side and a second side and further is fixed essentially near the first end and said inside surface of the said elongated hollow barrel and further extends inward toward the said longitudinal axis of the said elongated hollow barrel;

a slideable piston shatter plate with a first side and a second side, wherein said slideable piston shatter plate extends from said second side of said slideable piston flange to said first side of said elongated hollow barrel flange, and wherein said second side of said slideable piston flange is pressed against said first side of said slideable piston shatter plate and said second side of said slideable piston shatter plate is further pressed against said first side of said elongated hollow barrel flange further forming a fluid tight and a gas tight connection;

a spring, wherein said spring is compressed between said inside of said first barrel flange and said first side of said slideable piston flange and wherein said spring is disposed on said outside of said guide tube and wherein said spring is further thrusting on said slideable piston flange and wherein said slideable piston flange is thrusting on said slideable piston shatter plate and wherein said slideable piston shatter plate is thrusting on said elongated hollow barrel flange;

an elongated hollow plunger inside of said elongated hollow barrel, said elongated hollow plunger having a first end and a second end and further having an inside and an outside and further having a sliding gasket formed around the said outside of the said first end of said elongated hollow plunger, wherein said sliding gasket further forms a liquid and gas tight seal between said inside surface of said elongated hollow barrel and said outside of said elongated hollow plunger and wherein said elongated hollow plunger further has a thumb flat formed at said second end of said elongated hollow plunger;

a plunger shatter plate with a first side and a second side, wherein said plunger shatter plate is suitably fixed to said first end of said elongated hollow plunger at the said second side of said plunger shatter plate wherein a liquid and gas tight seal is formed between said elongated hollow plunger and said plunger shatter plate and wherein said elongated hollow plunger is pushed in a needle cannula direction by a said finger or thumb forcing said medicament or fluid through said cannula of said slideable piston and through said needle cannula and into said body or part of said body wherein said elongated hollow plunger is further pushed in a needle cannula direction thrusting said plunger shatter plate into said slideable piston flange further causing said plunger shatter plate to shatter and wherein said first end of said elongated hollow plunger is further thrust into said slideable piston shatter plate further causing said slideable piston shatter plate to shatter or fail wherein said slideable piston shatter plate can no longer restrain said slideable piston and said slideable piston flange and said compressed spring and wherein said compressed spring further thrusts said slideable piston flange fixed to said slideable piston and said needle cannula in the thumb flat direction into said elongated hollow plunger wherein said needle cannula is completely enclosed within said inner surface of said elongated hollow plunger and said thumb flat and is further prevented from exiting said elongated hollow plunger by the length of the expanded spring that is now greater than the combined length of said needle cannula and said slideable piston wherein said needle cannula cannot accidentally prick or injure anyone.

2. The syringe assembly of claim 1 wherein said slideable piston shatter plate has V grooves cut into said slideable piston shatter plate wherein said V grooves will enable said slideable piston shatter plate to shatter more easily.

3. The syringe assembly of claim 1 wherein said slideable piston flange is fixed to said slideable piston shatter plate by adhesive.

4. The syringe assembly of claim 1 wherein a gasket is placed between said slideable piston flange and said slideable piston shatter plate.

5. The syringe assembly of claim 1 wherein said slideable piston, said slideable piston flange and said slideable piston shatter plate are made in one piece.

6. The syringe assembly of claim 1 wherein said slideable piston shatter plate is made out of glass.

7. The syringe assembly of claim 1 wherein said slideable piston shatter plate is made out of plastic.

8. The syringe assembly of claim 1 wherein said elongated hollow barrel flange and said slideable piston shatter plate are made in one piece.

9. The syringe assembly of claim 1 wherein said slideable piston shatter plate is fixed to said elongated hollow barrel flange with a suitable adhesive.

10. The syringe assembly of claim I wherein said plunger shatter plate is made out of glass.

11. The syringe assembly of claim 1 wherein said plunger shatter plate and said elongated hollow plunger are one and the same part.

12. The syringe assembly of claim 1 wherein said plunger shatter plate is made out of plastic.

13. The syringe assembly of claim I wherein said guide tube laterally guides said slideable piston as said slideable piston is being thrust into said elongated hollow plunger wherein said slideable piston cannot move laterally in said guide tube, thereby further preventing said needle cannula from touching said inside surface of said guide tube near said first end of said guide tube thereby preventing any contamination from body fluids on said needle cannula from being rubbed off of said needle cannula near said first end of said guide tube and further preventing any accident or spread of diseases even from the outside of said syringe assembly.

14. A syringe assembly held by fingers and thumb for injecting medicament or fluid into a body or part of a body comprising:

a needle cannula with a first end and a second end, wherein there is a point at said first end and wherein there is a cannula formed in said needle cannula that extends from said first end through said second end;

a slideable piston with a first end and a second end, wherein said second end of said needle cannula is fixed to said first end of said slideable piston and wherein said slideable piston further has a cannula formed in said slideable piston, whereby said cannula extends from said first end of said slideable piston through said second end of said slideable piston and is further connected with said cannula of said needle cannula;

a slideable piston flange, wherein said slideable piston flange has a first side and a second side and wherein said first side of said slideable piston flange is fixed to said second end of said slideable piston, and wherein a cannula is formed in said slideable piston flange that aligns with said cannula in said slideable piston and wherein said cannula in said slideable piston flange extends from said first side through said second side of said slideable piston flange;

a first barrel flange with an inside and an outside, whereas said outside of said first barrel flange is nearer to said needle cannula and wherein an opening is formed in said first barrel flange wherein said opening extends from said inside of said first barrel flange through said outside of said first barrel flange and wherein said opening is greater in section than said slideable piston;

a first barrel with a first end and a second end, wherein said first end of said first barrel is fixed to said second side of said first barrel flange;

an elongated hollow barrel with a first end and a second end and an inside surface and an outside surface, wherein said elongated hollow barrel is suitably fixed to said second end of said first barrel at said first end of said elongated hollow barrel and wherein said elongated hollow barrel further has a longitudinal axis in the center of said elongated hollow barrel;

an elongated hollow barrel flange with a first side and a second side and further is fixed essentially near the said first end and said inside surface of the said elongated hollow barrel and further extends inward toward the said longitudinal axis of the said elongated hollow barrel;

a slideable piston shatter plate with a first side and a second side, wherein said slideable piston shatter plate extends from said second side of said slideable piston flange to said first side of said elongated hollow barrel flange, and wherein said second side of said slideable piston flange is pressed against said first side of said slideable piston shatter plate and said second side of said slideable piston shatter plate is further pressed against said first side of said elongated hollow barrel flange further forming a fluid tight and a gas tight connection.

a spring, wherein said spring is compressed between said inside of said first barrel flange and said first side of said slideable piston flange wherein said spring is further thrusting on said slideable piston flange and wherein said slideable piston flange is thrusting on said slideable piston shatter plate and wherein said slideable piston shatter plate is thrusting on said elongated hollow barrel flange;

an elongated hollow plunger inside of said elongated hollow barrel, said elongated hollow plunger having a first end and a second end and further having an inside and an outside and further having a sliding gasket formed around the said outside of the said first end of said elongated hollow plunger wherein said sliding gasket further forms a liquid and gas tight seal between said inside surface of said elongated hollow barrel and said outside of said elongated hollow plunger and wherein said elongated hollow plunger further has a thumb flat formed at said second end of said elongated hollow plunger;

a plunger shatter plate with a first side and a second side, wherein said plunger shatter plate is suitably fixed to said first end of said elongated hollow plunger at the said second side of said plunger shatter plate wherein a liquid and gas tight seal is formed between said elongated hollow plunger and said plunger shatter plate and wherein said elongated hollow plunger is pushed in a needle cannula direction, by a said finger or thumb forcing the said medicament or fluid through the said cannula of the said slideable piston and through said needle cannula and into said body or part of said body wherein said elongated hollow plunger is further pushed in a needle cannula direction thrusting said plunger shatter plate into said slideable piston flange further causing said plunger shatter plate to shatter and fail and wherein said first end of said elongated hollow plunger is further thrust into said slideable piston shatter plate further causing said slideable piston shatter plate to shatter or fail wherein said slideable piston shatter plate can no longer restrain said slideable piston and said slideable piston flange and said compressed spring and wherein said compressed spring further thrusts said slideable piston flange fixed to said slideable piston and said needle cannula in a thumb flat direction into said elongated hollow plunger wherein said needle cannula is completely enclosed within the said inner surface of said elongated hollow plunger and said thumb flat and is further prevented from exiting said elongated hollow plunger by the length of the expanded spring that is now greater than the combined length of said needle cannula and said slideable piston wherein said needle cannula cannot accidentally prick or injure anyone.

15. A syringe assembly held by fingers and thumb for injecting medicament or fluid into a body or part of a body comprising:

a needle cannula with a first end and a second end, wherein there is a point at said first end and wherein there is a cannula formed in said needle cannula that extends from said first end through said second end;

a slideable piston with a first end and a second end, wherein said second end of said needle cannula is fixed to said first end of said slideable piston and wherein said slideable piston further has a cannula formed in said slideable piston said cannula extends from said first end of said slideable piston through said second end of said slideable piston and is further aligned with said cannula of said needle cannula;

a slideable piston flange with a first side and a second side, Wherein said first side of said slideable piston flange is fixed to said second end of said slideable piston, and wherein a cannula is formed in said slideable piston flange that aligns with said cannula in said slideable piston and wherein said cannula in said slideable piston flange extends from said first side through said second side of said slideable piston flange;

a guide tube with a first end and a second end and an inside surface and an outside surface, wherein said slideable piston is held by said inside surface of said guide tube and said slideable piston is laterally supported by said inside surface of said guide tube and wherein said second end of said guide tube is near said slideable piston flange;

a first barrel flange with an inside and an outside, whereas said inside of said first barrel flange is fixed to said first end of said guide tube and said outside of said first barrel flange is nearer to said needle cannula;

a first barrel with a first end and a second end, wherein said first end of said first barrel is fixed to said inside of said first barrel flange;

an elongated hollow barrel with a first end and a second end and an inside surface and an outside surface, wherein said elongated hollow barrel is suitably fixed to said second end of said first barrel at said first end of said elongated hollow barrel and wherein said elongated hollow barrel further has a longitudinal axis in the center of said elongated hollow barrel;

an elongated hollow barrel flange with a first side and a second side and further is fixed essentially near the said first end and said inside surface of the said elongated hollow barrel and further extends inward toward the said longitudinal axis of the said elongated hollow barrel;

a slideable piston shatter plate with a first side and a second side, wherein said slideable piston shatter plate extends from said second side of said slideable piston flange to said first side of said elongated hollow barrel flange, and wherein said second side of said slideable piston flange is pressed against said first side of said slideable piston shatter plate and said second side of said slideable piston shatter plate is further pressed against said first side of said elongated hollow barrel flange further forming a fluid tight and a gas tight connection;

a spring, wherein said spring is compressed between said inside of said first barrel flange and said first side of said slideable piston flange and wherein said spring is disposed on the said outside of said guide tube and wherein said spring is further thrusting on said slideable piston flange and wherein said slideable piston flange is thrusting on said slideable piston shatter plate and wherein said slideable piston shatter plate is thrusting on said elongated hollow barrel flange;

an elongated hollow plunger inside of said elongated hollow barrel, said elongated hollow plunger having a first end and a second end and further having an inside and an outside and further having a sliding gasket formed around the said outside of the said first end of said elongated hollow plunger wherein said sliding gasket further forms a liquid and gas tight seal between said inside surface of said elongated hollow barrel and said outside of said elongated hollow plunger and wherein said elongated hollow plunger has a thumb flat at said second end of said elongated hollow plunger further closing said second end of said elongated hollow plunger;

a plunger hook rim with a sloping side fixed to said outside at said first end of said elongated hollow plunger, wherein said plunger hook rim has a first end and a second end and wherein said hook rim at least partially extends circumferentially around said first end of said elongated hollow plunger and wherein said hook rim further slopes from said first end and outside of said elongated hollow plunger toward said elongated hollow barrel and said second end of said hook rim and at said second end of said hook rim said hook rim is near perpendicular to and intersects said outside surface of said elongated hollow plunger;

a plunger shatter plate with a first side and a second side, wherein said plunger shatter plate is suitably fixed to said first end of said elongated hollow plunger at the said second side of said plunger shatter plate wherein a liquid and gas tight seal is formed between said elongated hollow plunger and said plunger shatter plate and wherein said elongated hollow plunger is pushed in a needle cannula direction, by a said finger or thumb forcing the said medicament or fluid through the said cannula of the said slideable piston and through said cannula of said needle cannula and into said body or part of said body wherein said elongated hollow plunger is further pushed in a needle cannula direction, thrusting said sloping side of said plunger hook rim past said elongated hollow barrel flange and further causing said second end of said hook rim to hook on said first side of said elongated hollow barrel flange wherein said hook rim is further locked onto said elongated hollow barrel flange and cannot be pulled off thereby further preventing said elongated hollow plunger from being withdrawn from said elongated hollow barrel without further destroying either said elongated hollow barrel or said elongated hollow plunger, and wherein said elongated hollow plunger is simultaneously thrusting said plunger shatter plate into said slideable piston flange further causing said plunger shatter plate to shatter and or fail wherein said first end of said elongated hollow plunger is further thrust into said slideable piston shatter plate further causing said slideable piston shatter plate to shatter or fail wherein said slideable piston shatter plate can no longer restrain said slideable piston and said slideable piston flange and said compressed spring and wherein said compressed spring further thrusts said slideable piston flange fixed to said slideable piston and said needle cannula in a thumb flat direction into said elongated hollow plunger and possibly into said thumb flat wherein said needle cannula is completely enclosed within said inside of said elongated hollow plunger and said thumb flat and is further prevented from exiting said elongated hollow plunger by the length of the expanded spring that is now greater than the combined length of said needle cannula and said slideable piston and wherein said elongated hollow plunger cannot be removed from said elongated hollow barrel wherein said needle cannula cannot be released or exposed and therefore cannot accidentally prick or injure anyone.

* * * * *